US012766238B2

(12) United States Patent
Oh

(10) Patent No.: US 12,766,238 B2
(45) Date of Patent: Oct. 20, 2026

(54) ABSORBER MODULE TO PREVENT DEVICE CONTAMINATION BY SECRETION

(71) Applicants: GENEONE LIFE SCIENCE, INC., Seoul (KR); CUBIST CO., LTD., Seoul (KR)

(72) Inventor: Young Woo Oh, Seoul (KR)

(73) Assignees: GENEONE LIFE SCIENCE, INC., Seoul (KR); CUBIST CO., LTD., Seoul (KR)

( * ) Notice: Subject to any disclaimer, the term of this patent is extended or adjusted under 35 U.S.C. 154(b) by 393 days.

(21) Appl. No.: 18/284,300

(22) PCT Filed: Apr. 13, 2022

(86) PCT No.: PCT/KR2022/005362

§ 371 (c)(1), (2) Date: Sep. 27, 2023

(87) PCT Pub. No.: WO2022/220589

PCT Pub. Date: Oct. 20, 2022

(65) Prior Publication Data

US 2024/0165315 A1 May 23, 2024

(30) Foreign Application Priority Data

Apr. 14, 2021 (KR) ........................ 10-2021-0048441

(51) Int. Cl.
*A61M 1/00* (2006.01)

(52) U.S. Cl.
CPC ......... *A61M 1/78* (2021.05); *A61M 2205/125* (2013.01); *A61M 2205/7527* (2013.01); *A61M 2210/04* (2013.01)

(58) Field of Classification Search
CPC .............. A61M 1/78; A61M 2205/125; A61M 2205/7527; A61M 2210/04; A61M 1/64;
(Continued)

(56) References Cited

U.S. PATENT DOCUMENTS 3,965,902 A * 6/1976 Reilly ..................... A61M 1/60 604/320
2001/0041848 A1* 11/2001 Ito ........................ A61M 1/7411 601/6
(Continued)

FOREIGN PATENT DOCUMENTS

JP 2007222207 A * 9/2007
KR 10-1995-0004739 A 2/1995
(Continued)

OTHER PUBLICATIONS

Cambridge Dictionary, Eccentric | definition in the Cambridge Dictionary, 2025, https://dictionary.cambridge.org/us/dictionary/english/eccentric (Year: 2025).*
(Continued)

*Primary Examiner* — Kai H Weng
*Assistant Examiner* — Katherine-Ph Minh Pham
(74) *Attorney, Agent, or Firm* — Revolution IP, PLLC

(57) ABSTRACT

The present invention relates to an absorber module to prevent device contamination by a secretion, and more particularly, to an absorber module to prevent device contamination by a secretion, which includes a housing having an absorption module therein and including an adjustment unit capable of adjusting an absorption strength on an outer surface thereof, an absorption unit connected to an upper end of a body portion and absorbing waste products such as sebum and blackheads on a skin surface, and a ring-shaped first packing unit and a ring-shaped second packing unit disposed at an upper end of the first packing unit and detachable from the first packing unit.

11 Claims, 6 Drawing Sheets

(58) Field of Classification Search
CPC .................... A61B 17/00; A61B 17/50; A61B 2017/00561; A61B 2017/00747; A61B 2217/005
See application file for complete search history.

(56) References Cited

U.S. PATENT DOCUMENTS

| | | | | |
|---|---|---|---|---|
| 2002/0128663 | A1 | 9/2002 | Mercier et al. | |
| 2015/0080667 | A1* | 3/2015 | Bahr | A61M 1/7411 600/249 |
| 2017/0202579 | A1* | 7/2017 | Abrahams | A61M 1/79 |
| 2019/0357931 | A1* | 11/2019 | Xia | A61B 17/1155 |

FOREIGN PATENT DOCUMENTS

| | | | |
|---|---|---|---|
| KR | 20-0126177 | Y1 | 9/1998 |
| KR | 10-2009-0011745 | A | 2/2009 |
| KR | 10-2214386 | B1 | 2/2021 |

OTHER PUBLICATIONS

Cambridge Dictionary, Panel | definition in the Cambridge Dictionary, 2025, https://dictionary.cambridge.org/us/dictionary/english/panel (Year: 2025).*
International Search Report for PCT/KR2022/005362 mailed Aug. 1, 2022 from Korean Intellectual Property Office.

* cited by examiner (A)

(B)

(A) (B)

(A) (B)

(A) (B)

ABSORBER MODULE TO PREVENT DEVICE CONTAMINATION BY SECRETION

TECHNICAL FIELD

The present invention relates to an absorber module to prevent device contamination by a secretion, and more particularly, to an absorber module to prevent device contamination by a secretion, which includes a housing having an absorption module therein and including an adjustment unit capable of adjusting an absorption strength on an outer surface thereof, an absorption unit connected to an upper end of a body part and absorbing waste products such as sebum and blackheads on a skin surface, and a ring-shaped first packing unit and a ring-shaped second packing unit disposed at an upper end of the first packing unit and detachable from the first packing unit.

BACKGROUND ART

Contents described in this section merely provide background information on the present invention and do not constitute the related art.

In recent times, as living standards have improved and women's social advancement has become more active, continuous skin care are frequently received to not only treat dead skin cells, freckles, stains and acne on the skin, but also to tighten sagging skin and have wrinkle-free skin, and professional management offices that make this their business are spreading rapidly.

This ultimately means that in recent times, the skin care is no longer treated as a form of extravagance and luxury. Moreover, even in the case of ordinary people who are not engaged in a specific broadcasting entertainment industry, regardless of gender or age, they are trying various skin care methods to maintain young and elastic skin to create their own unique personality or to gain confidence in others.

The conventional absorber module discloses a structure that includes a handpiece that can be held in the hand, a tip that is mounted on the tip of the handpiece and contacts the skin, and a dome-shaped absorption unit with an open lower part inside the tip.

The conventional absorber module is a device that removes dead skin cells from the face, injects a nutrient solution for skin regeneration into the skin, and applies low frequencies to the skin to improve the skin and regenerate cells.

Furthermore, when the tip is brought into contact with the skin after cleansing in order to remove dead skin cells and foreign substances while supplying nutrients to the skin of the recipient, not only is skin wrinkles improved by absorbing foreign substances on the skin surface through the absorption unit, but also the skin cells are stimulated and regenerated.

In addition, the nutrients of the face wash are injected deep into the skin through the irritated skin to have a skin massage effect, and the negative pressure applied through an absorption port is applied to the absorption unit through the absorption hole to pull the skin and perform a massage.

However, a problem has been pointed out in the conventional absorber module that during massage using negative pressure, cleansing liquid, dead skin cells, or foreign substances flow through the wall of the absorption unit into an absorption hole, causing frequent blockage of the absorption hole or inlet.

In order to solve the problems of the conventional absorber module mentioned above, some domestic and foreign related companies have conducted research on absorber modules that limit a shape of a cap, but for actual production, as it is necessary to have a limited structure of the cap, the cost may be excessive, or even if not, the effect compared to the manufacturing cost of the device is not large, so the market competitiveness is low compared to the conventional absorber modules, and no cases of full-scale commercialization have been found.

Therefore, there is a need for the development of an absorber module that prevents device contamination by a secretion that can solve the problems of the prior art as described above.

DISCLOSURE OF THE INVENTION

Technical Goals

The problem to be solved by the present invention is to make up for the shortcomings of the prior art mentioned above, and objects of the present invention are as follows.

First, the present invention is to provide an absorber module to prevent device contamination by a secretion that can be continuously cleaned by removing and cleaning a cap contaminated by skin foreign substances.

Second, the present invention is to provide an absorber module to prevent contamination of the device by a secretion, which improves the feeling of operation by a button unit having a shape corresponding to the shape of a finger of a user, and can easily adjust an absorption strength by a plurality of panel units supporting the button unit.

The objects of the present invention are not limited to the aforementioned objects, and other objects, which are not mentioned above, will be clearly understood to those skilled in the art from the following description.

Technical Solutions

According to the present invention, provided is an absorber module to prevent device contamination by a secretion, which includes: a housing including an absorption module therein and an adjustment unit capable of adjusting an absorption strength on an outer surface thereof; an absorption unit connected to a top of a body part and absorbing waste products such as sebum and blackheads on a skin surface; and a cap blocking external substances from entering the absorption unit by covering the outer surface of the absorption unit to prevent the absorption unit from being contaminated by the external substances, and detachable from the top of the absorption unit.

In this case, the cap may include a body part coupled to and detachable from the side of the absorption unit, and having an external surface which is knurled, and a head part formed to extend from an upper surface of the body part and, when fastened to the absorption unit, being spaced apart from the top of the absorption unit at a predetermined distance.

Furthermore, the head part may include a ring-shaped first packing portion extending from the top of the body part, and a ring-shaped second packing portion disposed on the top of the first packing portion, and detachable from the first packing portion.

Further, the second packing portion may include a coupling protrusion protruding from a lower surface of the second packing portion to improve a fastening force between the first packing portion and the second packing portion by primarily increasing a contact surface area between the first packing portion and the second packing portion.

Meanwhile, the second packing portion may include an elastic portion disposed between the second packing portion and the coupling protrusion to prevent the second packing portion from being damaged by impact generated during attachment and detachment.

In this case, the elastic portion may include a protrusion portion protruding from a lower surface of the elastic portion to improve the fastening force between the first packing portion and the second packing portion by secondarily increasing the contact surface area between the first packing portion and the second packing portion, and the first packing portion may include a receiving groove disposed on the upper surface of the first packing portion to receive the protrusion portion.

Further, the protrusion portion may have a predetermined slope to improve the fastening force between the first packing portion and the second packing portion by tertiarily increasing the contact surface area between the first packing portion and the second packing portion, and the receiving groove may have a slope corresponding to the slope of the protrusion portion so that the protrusion portion may be inserted therein.

According to another feature of the present invention, the adjustment unit may include a button part capable of selectively adjusting the absorption strength of the absorption unit for each step by the user's pressure operation, and a panel part disposed on the lower surface of the button part to support the button part.

In this case, the button part may include a first eccentric portion in which a height of the button part gradually increases from the center of the button to the outer surface for the user's convenience of operation, and a second eccentric portion in which a height of the button part gradually decreases from the outer surface of the first eccentric portion to the outer surface so as to induce the user to press the first eccentric portion.

Furthermore, the second eccentric portion may have a shape in which a width gradually decreases downwards from the upper surface of the button part with a longitudinal direction of the button part as an axis so as to prevent the button part and the housing from being damaged due to friction as the button part is pressed by the user.

Further, the panel part may include a first panel disposed on the lower surface of the button part to support the button part and primarily prevent external substances from entering the housing, and a second panel disposed on the lower surface of the first panel to secondarily prevent external substances from entering the housing, and a third panel disposed on the lower surface of the second panel to support the first panel and the second panel.

Meanwhile, the first panel may include a first transmission unit protruding from the lower surface of the first panel to primarily transmit the pressure pressed downward to the button part by the user to an adjustment module, and the second panel may include a second transmission unit engraved from the lower surface of the second panel to secondarily transmit the pressure pressed downward to the first transmission unit to the adjustment module.

In this case, the first panel may include a guider protruding from the side of the first panel so that the first panel and the second panel may be fastened in a predetermined coupling direction, and the second panel may include a guider receiving portion protruding from the side of the second panel to receive the guider.

Furthermore, the third panel may include multiple coupling grooves protruding from the side of the third panel so as to be coupled and fixed to the adjustment module and including a receiving space into which a coupling member, etc., may be inserted.

Additional solutions of the present invention will be partially explained in the description that follows below, and may be partially and easily identified from the description, or may be learned by practicing the present invention.

Both the foregoing general description and the following detailed description are exemplary and explanatory only and do not limit the present invention as set forth in the claims.

Advantageous Effects

Effects of the present invention, which are configured as above are described as below.

First, by separating the cap contaminated with skin foreign substances after skin care into a first packing unit and a second packing unit, continuous cleanliness management is possible by cleaning each unit of the cap.

Second, by a button unit having a shape corresponding to the shape of finger of a user, the feeling of operation is improved, and an absorption strength is easily adjusted by a plurality of panel units supporting the button unit.

The effects of the present invention are not limited to the aforementioned effects, and other effects, which are not mentioned above, will be apparently understood to those skilled in the art from the description of the claims.

DETAILED DESCRIPTION

Figure 1:
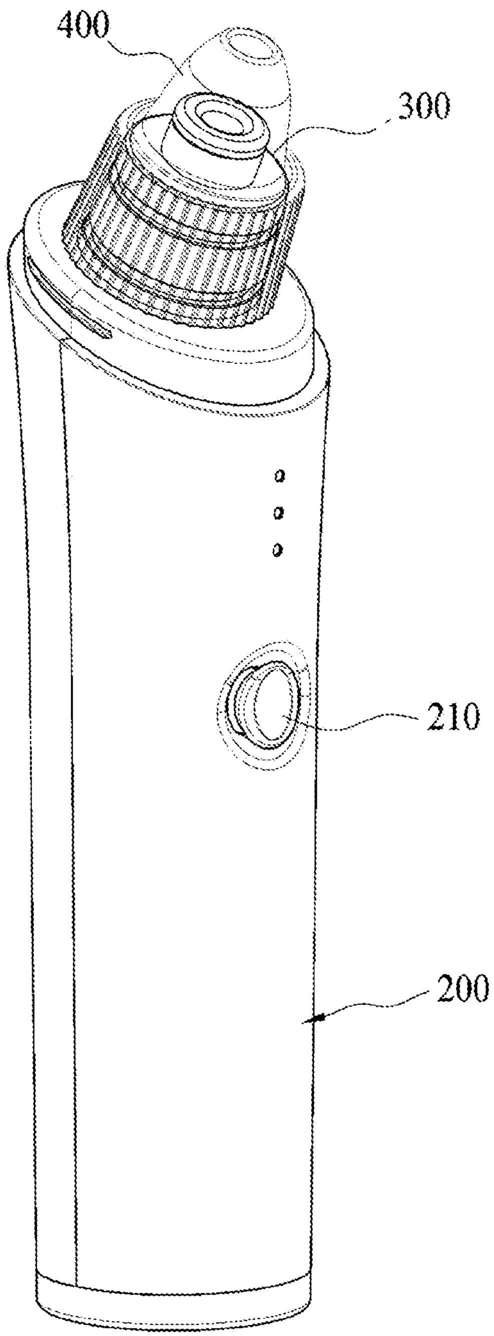
FIG. 1 is a perspective view of an absorber module to prevent device contamination by a secretion according to an embodiment of the present invention.

Hereinafter, specific embodiments of the present invention will be described in detail with reference to the accompanying drawings.

Further, in describing a specific embodiment of the present invention, detailed description of associated known function or constitutions will be omitted if it is determined that they unnecessarily make the gist of the present invention unclear.

The aforementioned objects, features, and advantages of the present invention will be clearer through the following detailed description associated with the accompanying drawings. However, the present invention may have various modifications and include various embodiments, so hereinafter, specific embodiments will be illustrated in the drawings and described in detail.

In describing the present invention, a detailed explanation of known related functions or constitutions may be omitted to avoid unnecessarily obscuring the gist of the present invention. Additionally, numbers used in the description process of this specification are merely identification symbols to distinguish one component from another component.

Further, suffix "unit" for components used in the following description is given or mixed in consideration of easy preparation of the present invention only and does not have their own distinguished meanings or roles.

FIG. 1 is a perspective view of an absorber module to prevent device contamination by a secretion according to an embodiment of the present invention.

The absorber module to prevent device contamination by a secretion according to an embodiment of the present invention may include a housing 200, an absorption unit 300, and a cap 400.

The housing 200 may be provided with an absorption module therein.

The housing 200 may include an adjustment unit 210 that may adjust an absorption strength.

The housing 200 may be formed by a rigid body whose shape does not change (for example, metal such as iron, aluminum, copper, etc., or synthetic resins such as polystyrene (PS), ABS, polyacetal (POM), polyethylene (PE), polyvinyl chloride (PVC), polycarbonate (PC), polycaprolactone (PCL), and polypropylene (PP) may be selected).

The absorption unit 300 may be connected to the top of a body part 410 and may absorb waste products such as sebum and blackheads on a skin surface.

The cap 400 may block external substances from entering the absorption unit 300 by covering the outer surface of the absorption unit 300 to prevent the absorption unit 300 from being contaminated by the external substances.

The cap 400 may be attached to the top of the absorption unit 300 and may be separated from the top of the absorption unit 300.

Figure 2:
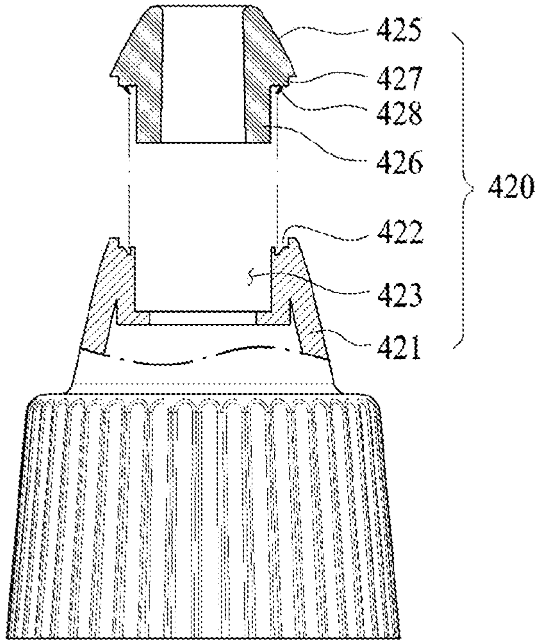
FIG. 2 is a detailed view of a cap according to an embodiment of the present invention.

FIG. 2 is a detailed view of the cap 400 according to an embodiment of the present invention.

The cap 400 may include a body part 410 and a head part 420.

The body part 410 is coupled to and detachable from the side of the absorption unit 300, and an outer surface thereof may be knurled for improved grip feeling.

The head part 420 is formed to extend from an upper surface of the body part 410 and, when fastened to the absorption unit 300, may be spaced apart from the top of the absorption unit 300 at a predetermined distance.

The head part 420 may include a first packing portion 421 and a second packing portion 425.

The first packing portion 421 may extend from the top of the body part 410 and may have a ring shape.

The second packing portion 425 may be disposed at the top of the first packing portion 421 and detachable from the first packing portion 421, and may have the ring shape.

The second packing portion 425 may include a coupling protrusion 426 and an elastic portion 427.

As a contact surface area between the first packing portion 421 and the second packing portion 425 primarily increases, the coupling protrusion 426 may protrude from a lower surface of the second packing portion 425 to improve a fastening force between the first packing portion 421 and the second packing portion 425.

A filter (not shown) may be coupled to the lower surface of the coupling protrusion 426. The shape of the filter may be a grid or other known shapes.

A bulky secretion other than skin waste may be introduced into the housing 200 by the absorption unit 300. The bulky secretion may cause malfunction and damage to the absorber module. The absorber module according to an embodiment of the present invention may prevent the malfunction and the damage of the device by placing the filter between the first packing portion 421 and the second packing portion 425 to prevent external substances other than the skin waste from entering.

Furthermore, a filter portion is detached from the second packing portion 425, so there is an advantage in hygiene management by cleaning the filter portion or replacing the filter portion with a new filter.

The elastic portion 427 may be disposed between the second packing portion 425 and the coupling protrusion 426 to prevent the second packing portion 425 from being damaged by impact generated during attachment and detachment.

The elastic portion 427 may include a protrusion portion 428.

As the contact surface area between the first packing portion 421 and the second packing portion 425 secondarily increases, the protrusion portion 428 may protrude from a lower surface of the elastic portion 427 to improve the fastening force between the first packing portion 421 and the second packing portion 425.

As the contact surface area between the first packing portion 421 and the second packing portion 425 tertiarily increases, so the protrusion portion 428 may have a predetermined slope to improve the fastening force between the first packing portion 421 and the second packing portion 425.

The first packing portion 421 may include a receiving groove 422.

The receiving groove 422 may be disposed on the upper surface of the first packing portion 421 to receive the protrusion portion 428.

The receiving groove 422 may have a slope corresponding to the slope of the protrusion portion 428 so that the protrusion portion 428 may be inserted therein.

Figure 3:
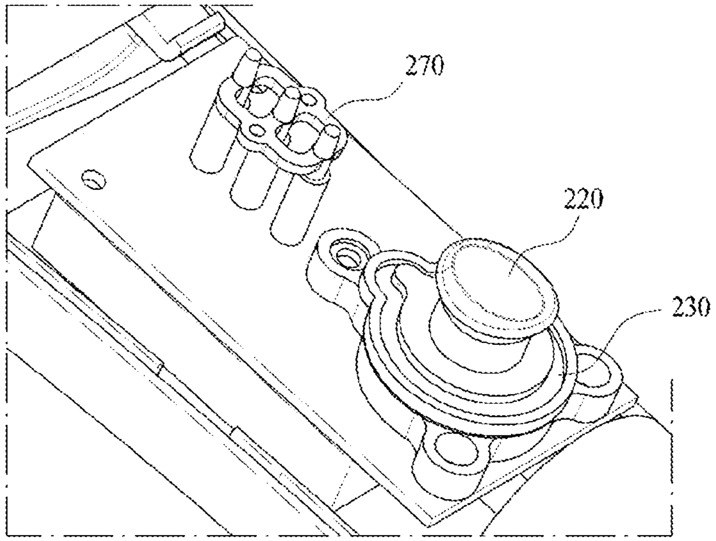
FIG. 3 is a perspective view of an adjustment unit according to an embodiment of the present invention.

FIG. 3 is a perspective view of the adjustment unit 210 according to an embodiment of the present invention.

The adjustment unit 210 may include a button part 220 and a panel part 230.

The button part 220 may selectively adjust the absorption strength of the absorption unit 300 for each step by the user's pressure operation.

The panel part 230 may be disposed on the lower surface of the button part 220 to support the button part 220.

Figure 4:
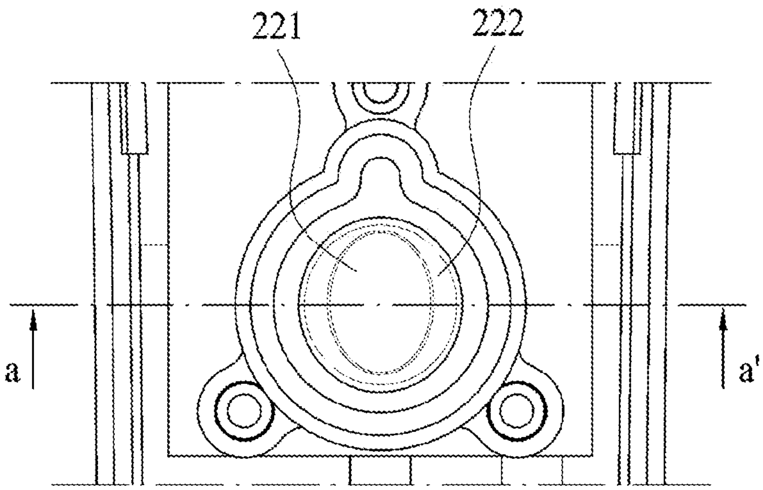
FIG. 4 is a detailed view of a button unit according to an embodiment of the present invention.
Figure 4:
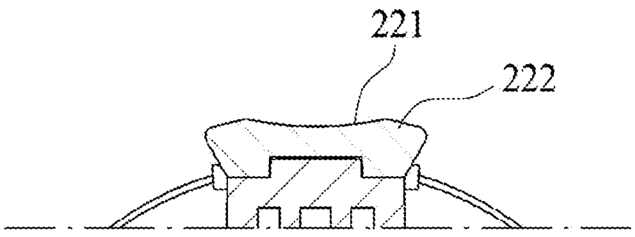

FIG. 4 is a detailed view of the button part 220 according to an embodiment of the present invention.

The button part 220 may include a first eccentric portion 221 and a second eccentric portion 222.

As shown in FIG. 4B, the first eccentric portion 221 may be formed in a shape in which a height of the button part 220 gradually increases from the center of the button to the outer surface for the user's convenience of operation.

As shown in FIG. 4B, the second eccentric portion 222 may be formed in a shape in which a height of the button part 220 gradually decreases from the outer surface of the first eccentric portion 221 to the outer surface so as to induce the user to press the first eccentric portion 221.

As shown in FIG. 4A, the first eccentric portion 221 and the second eccentric portion 222 may have an oval shape, but alternatively, they may have a circular shape, and may have other known shapes such as a triangle, a square, etc.

The side of the second eccentric portion 222 may have a shape in which a width gradually decreases downwards from the upper surface of the button part 220 with a longitudinal direction of the button part 220 as an axis as shown in FIG. 4B.

As a result, the button part 220 and the housing 200 may be prevented from being damaged due to friction as the button part 220 is pressed by the user.

FIG. 5 is an exploded view of the panel part 230 according to an embodiment of the present invention.

The panel part 230 may include a first panel 240, a second panel 250, and a third panel 260.

The first panel 240 may be disposed on the lower surface of the button part 220 to support the button part 220 and primarily prevent external substances from entering the housing 200.

The second panel 250 may be disposed on the lower surface of the first panel 240 to secondarily prevent external substances from entering the housing 200.

The third panel 260 may be disposed on the lower surface of the second panel 250 to support the first panel 240 and the second panel 250.

Figure 5A:
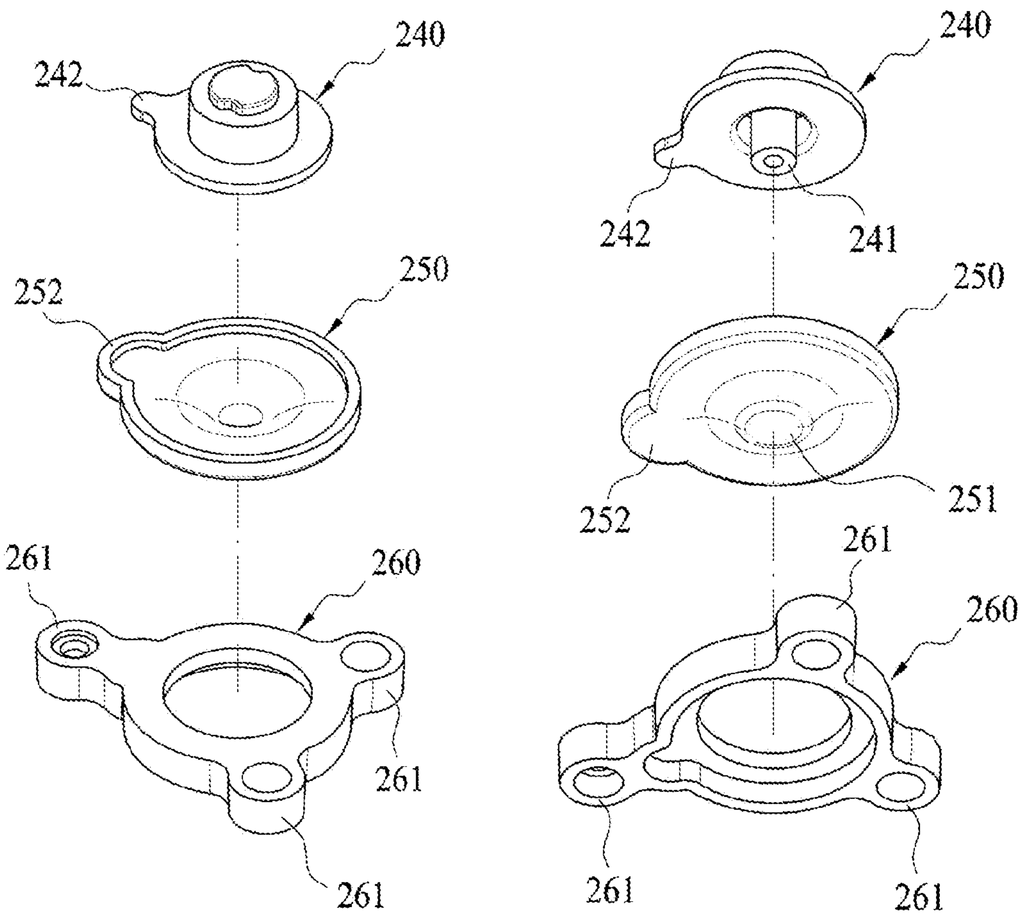
FIG. 5 is an exploded view of a panel unit according to an embodiment of the present invention.

As shown in FIG. 5A, the first panel 240, the second panel 250, and the third panel 260 may have the circular shape, but may have the oval shape unlike this, and may have other known shapes such as the triangle, the square, etc.

The first panel 240 may include a first transmission unit 241 and the second panel 250 may include a second transmission unit 251.

The first transmission unit 241 protrudes from the lower surface of the first panel 240, so that the pressure pressed downward to the button part 220 by the user may be transmitted primarily to the adjustment module 270.

The second transmission unit 251 is engraved from the lower surface of the second panel 250 as shown in FIG. 5B, so that the pressure pressed downward to the first transmission unit 241 may be secondarily transmitted to the adjustment module 270, but, unlike this, may be embossed from the upper surface of the second panel 250.

As a result, when the user presses the button part 220, as the pressure is sequentially applied from the button part 220 to the first panel 240, from the first panel 240 to the second panel 250, and from the second panel to the third panel 260, the user may feel a soft and sequential operation sense, and durability may be improved by preventing the malfunction of the button part 220.

The first panel 240 may include a guider 242, and the second panel 250 may include a guider receiving portion 252.

The guider 242 may protrude from the side of the first panel 240 so that the first panel 240 and the second panel 250 may be fastened in a predetermined coupling direction. The guider receiving portion 252 may protrude from the side of the second panel 250 to receive the guider 242.

As a result, when the first panel 240 and the second panel 250 are fastened in a direction in which the guider 242 is not inserted into the guider receiving portion 252, the first panel 240 and the second panel 250 are prevented from being coupled to each other to prevent the malfunction and the damage to the device. When the first panel 240 and the second panel 250 are fastened in a direction in which the guider 242 is inserted into the guider receiving portion 252, the guider 242 and the guider receiving portion 252 do not deviate from each other to fasten the first panel 240 and the second panel 250 to each other.

The third panel 260 may further include a coupling groove 261.

The coupling groove 261 protrudes from the side of the third panel 260 so as to be coupled and fixed to the adjustment module 270 and may include a receiving space into which a coupling member, etc., may be inserted, and multiple receiving spaces may be formed.

Figure 6:
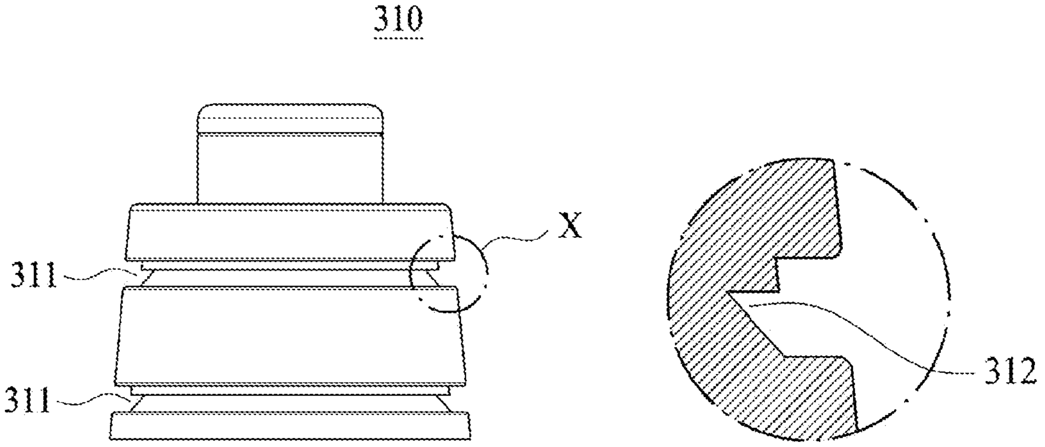
FIGS. 6 and 7 are detailed views of an absorption unit according to an embodiment of the present invention.
Figure 7:
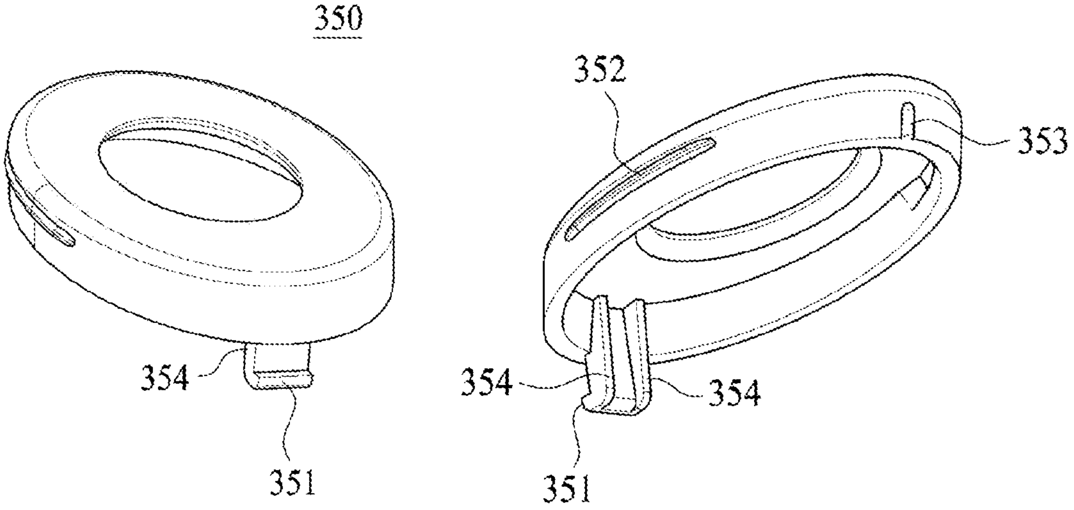

FIGS. 6 and 7 are detailed views of the absorption unit according to an embodiment of the present invention.

The absorption unit 300 may include an upper absorption unit 310 and a lower absorption unit 350.

The upper absorption unit 310 may include a first sliding groove 311 and a second sliding groove 312.

The first sliding groove 311 and the second sliding groove 312 may receive an adjustment protrusion (not shown) formed on an inner peripheral surface of the body part 410 of the cap 400.

As a result, the adjustment protrusion of the body part 410 is inserted into a first sliding groove 311 and sequentially inserted into a second sliding groove 312, as shown in FIG. 6B, so that the slope of the cap 400 may be adjusted. The cap 400 of the absorber module according to the present invention may be separated from the absorption unit 300, and the cap 400 may be inserted into the first sliding groove 311 or the second sliding groove 312 depending on the user's purpose to remove foreign substances on the skin surface.

The lower absorption unit 350 may include a catching part 351, a stopper 352, an auxiliary catching part 353, and a guide rail 354.

The catching part 351 may protrude from the lower surface of the lower absorption unit 350 and fixed to one side of the housing 100.

The stopper 352 may protrude from the side of the lower absorption unit 350 to prevent the absorption unit 300 from spinning after being fastened to the housing 100. Furthermore, one end of the stopper 352 is cut in an inclined shape to prevent damage due to wear.

The auxiliary catching part 353 may be disposed opposite to the catching part 351.

The guide rail 354 may protrude on the outer surface of the catching part 351 as shown in FIG. 7A, and may be engraved from the inner surface of the catching part 351 as shown in FIG. 7B. As a result, by inducing the direction in which the absorption unit 300 is fastened to the housing 100, the user may more easily attach or separate the absorption unit 300 from the housing 100 and manage the absorber module.

The embodiment merely illustratively describes the technical spirit of the present invention and various changes and modifications of the present invention can be made by those skilled in the art to which the present invention pertains without departing from an essential characteristic of the present invention.

The embodiment is only for illustrative purposes but not intended to limit the technical spirit of the present invention. Accordingly, the scope of the present invention is not limited to the embodiment.

The protection scope of the present invention should be construed based on the following appended claims and it should be appreciated that all technical spirits recognized as being equivalent to the claims belong to the scope of the present invention.

100—present invention
200—housing
210—adjustment unit
220—button part
221—first eccentric portion
222—second eccentric portion
230—panel part
240—first panel
241—first transmission unit
242—guider
250—second panel
251—second transmission unit

252—guider receiving portion
260—third panel
261—coupling groove
270—adjustment module
300—absorption unit
310—upper absorption unit
311—first sliding groove
312—second sliding groove
350—lower absorption unit
351—catching part
352—stopper
353—auxiliary catching part
354—guide rail
400—cap
410—body part
420—head part
421—first packing portion
422—receiving groove
423—receiving space
425—second packing portion
426—coupling protrusion
427—elastic portion
428—protrusion portion

The invention claimed is:

1. An absorber module to prevent device contamination by a secretion, comprising:
   a housing including an absorption module therein and an adjustment unit capable of adjusting an absorption strength on an outer surface thereof;
   an absorption unit connected to a top of a body part and absorbing waste products such as sebum and blackheads on a skin surface; and
   a cap blocking external substances from entering the absorption unit by covering the outer surface of the absorption unit to prevent the absorption unit from being contaminated by the external substances, and detachable from the top of the absorption unit,
   wherein the cap comprises:
   the body part coupled to and detachable from the side of the suction unit, and having an external surface which is knurled, and
   a head part formed to extend from an upper surface of the body part and, when fastened to the absorption unit, being spaced apart from the top of the absorption unit at a predetermined distance,
   wherein the head part comprises
   a ring-shaped first packing portion extending from the top of the body part, and
   a ring-shaped second packing portion disposed on the top of the first packing portion, and detachable from the first packing portion,
   wherein the second packing portion comprises a coupling protrusion protruding from a lower surface of the second packing portion to improve a fastening force between the first packing portion and the second packing portion by primarily increasing a contact surface area between the first packing portion and the second packing portion,
   wherein the second packing portion comprises an elastic portion disposed between the second packing portion and the coupling protrusion to prevent the second packing portion from being damaged by impact generated during attachment and detachment.

2. The absorber module to prevent device contamination by a secretion of claim 1, wherein the elastic portion comprises a protrusion portion protruding from a lower surface of the elastic portion to improve the fastening force between the first packing portion and the second packing portion by secondarily increasing the contact surface area between the first packing portion and the second packing portion, and
   the first packing portion comprises a receiving groove disposed on the upper surface of the first packing portion to receive the protrusion portion.

3. The absorber module to prevent device contamination by a secretion of claim 2, wherein the protrusion portion has a predetermined slope to improve the fastening force between the first packing portion and the second packing portion by tertiarily increasing the contact surface area between the first packing portion and the second packing portion, and
   the receiving groove has a slope corresponding to the slope of the protrusion portion so that the protrusion portion may be inserted therein.

4. The absorber module to prevent device contamination by a secretion of claim 1, wherein the adjustment unit comprises:
   a button part capable of selectively adjusting the absorption strength of the absorption unit for each step by a user's pressure operation, and
   a panel part disposed on the lower surface of the button part to support the button part.

5. The absorber module to prevent device contamination by a secretion of claim 4, wherein the button part comprises:
   a first eccentric portion in which a height of the button part gradually increases from the center of the button part to the outer surface for user's convenience of operation, and
   a second eccentric portion in which a height of the button part gradually decreases from the outer surface of the first eccentric portion to the outer surface so as to induce the user to press the first eccentric portion.

6. The absorber module to prevent device contamination by a secretion of claim 5, wherein the second eccentric portion has a shape in which a width gradually decreases downwards from the upper surface of the button part with a longitudinal direction of the button part as an axis so as to prevent the button part and the housing from being damaged due to friction as the button part is pressed by the user.

7. The absorber module to prevent device contamination by a secretion of claim 4, wherein the panel part comprises:
   a first panel disposed on the lower surface of the button part to support the button part and primarily prevent external substances from entering the housing, and
   a second panel disposed on the lower surface of the first panel to secondarily prevent external substances from entering the housing.

8. The absorber module to prevent device contamination by a secretion of claim 7, wherein the panel part further comprises a third panel disposed on the lower surface of the second panel to support the first panel and the second panel.

9. The absorber module to prevent device contamination by a secretion of claim 8, wherein the third panel comprises multiple coupling grooves protruding from the side of the third panel so as to be coupled and fixed to an adjustment module and including a receiving space into which a coupling member is inserted.

10. The absorber module to prevent device contamination by a secretion of claim 7, wherein the first panel comprises a first transmission unit protruding from the lower surface of the first panel to primarily transmit the pressure applied downward to the button part by the user to an adjustment module, and the second panel comprises a second transmission unit engraved from the lower surface of the second panel to secondarily transmit the pressure pressed downward to the first transmission unit to the adjustment module.

11. The absorber module to prevent device contamination by a secretion of claim 7, wherein the first panel comprises a guider protruding from the side of the first panel so that the first panel and the second panel may be fastened in a predetermined coupling direction, and the second panel comprises a guider receiving portion protruding from the side of the second panel to receive the guider.

* * * * *